(12) United States Patent
Walther et al.

(10) Patent No.: US 7,049,336 B2
(45) Date of Patent: *May 23, 2006

(54) METHOD FOR DIAGNOSING NEURONAL DISEASES AND FOR TREATING PRIMARY HEMOSTASIS DEFICIENCY

(75) Inventors: Diego Walther, Berlin (DE); Michael Bader, Berlin (DE)

(73) Assignee: Max-Delbruck-Centrum fur Molekulare Medizin (DE)

( * ) Notice: Subject to any disclaimer, the term of this patent is extended or adjusted under 35 U.S.C. 154(b) by 48 days.

This patent is subject to a terminal disclaimer.

(21) Appl. No.: 10/363,474

(22) PCT Filed: Aug. 27, 2001

(86) PCT No.: PCT/DE01/03178

§ 371 (c)(1),
(2), (4) Date: Jul. 22, 2003

(87) PCT Pub. No.: WO02/17891

PCT Pub. Date: Mar. 7, 2002

(65) Prior Publication Data

US 2004/0014656 A1    Jan. 22, 2004

(30) Foreign Application Priority Data

Aug. 31, 2000 (DE) ............................... 100 43 124

(51) Int. Cl.
*A61K 31/405* (2006.01)

(52) U.S. Cl. ..................................... 514/415; 548/504
(58) Field of Classification Search ................ 548/504; 514/415

See application file for complete search history.

(56) References Cited

U.S. PATENT DOCUMENTS

| 3,686,414 A | 8/1972 | Koe ........................... 424/319 |
| 4,994,475 A | 2/1991 | Gittos ........................ 514/348 |
| 2004/0097576 A1* | 5/2004 | Walther et al. ............. 514/419 |

FOREIGN PATENT DOCUMENTS

GB    2105192    3/1983

OTHER PUBLICATIONS

Raitano et al., 2004, CAS:140:230615.*

* cited by examiner

*Primary Examiner*—Taofiq Solola
*Assistant Examiner*—Robert Shiao
(74) *Attorney, Agent, or Firm*—Saliwanchik, Lloyd & Saliwanchik (57) ABSTRACT

Pharmaceutical compositions for treatment of primary hemostasis deficiency and methods of treatment of primary hemostasis deficiency are disclosed. Also, methods for diagnosing neuronal diseases and for suppressing the immune system are disclosed. Isoforms responsible for maintaining primary hemostasis, T-cell mediated immune responses, neuron specific TPH, and a neuronal tryptophan hydroxylase are disclosed.

8 Claims, 9 Drawing Sheets

```
.........ACACCACACGGCTGGGCAGGTTCTAGATTTGTGTACACACAAAT
                     ‾‾‾‾‾‾‾‾
                       SP1
            <CCAAT>
CCTTTATTAGCTAGGTGGTCATTGGGAGTGAATGTCTCTCTGCATGTCTCAAT
                    ‾‾‾‾‾
                    CTF/NF-Y

AAAATACGAGAGAACCCTGCCTCCCTCAGGCCATTAGGAATTGATAGTTAAAC
                              ‾‾‾‾
                              NF-1

TGTTTGAAGTGCTTGAGGTTGTACAAAGTAAACAGTCAATAAATGTTGACTAT
                     ‾‾‾‾‾‾‾
                     TFII-D
     +1 ?                     TATA-Box
CGTTATCAAGCGAGTTTGTGCTTCCC ATG ACA G  gttatttagtcattca
                                   A G gtaagt-Konsensus
     53 bp-Intron
aagaataaacatttgaatgtggacaccatcctcgaag GA CCC GAG ACT
       YNYRAY-Konsensus              Y_n cag G-Konsensus RT-PCR-Primer
AGG GCT CCT GCC ACA TG G CAG AGC CTT AGC CAA CTT CCT TTC AAC CTG TTT CTC TCC CTG ACT TCC TTG gtgaggagttataaaac
                                    AG gtaagt-Konsensus
```

B

```
        Exon 2b              Intron
                   AG gt aagt- consensus
                      |              genomic sequence
...TCCCTGA CTTCCTT G gt gaggagttat aa...   mouse
...AGCCTTA ACCTCCT G gt ctcaagtgac cc...   human
...TCCCTGA CCTCTTT A gt gaggagttat aa...   rat protein sequence
...SerLeuT hrSerLeu                    mouse and rat
...SerLeuA snLeuLeu                    human
```

```
  1 MTGPETRAPA TWQSLSQLPF NLFLSLTSLE NHVSLLHIES RKSKQRNSEF
 51 EIFVDCDISR EQLNDIFPLL KSHATVLSVD SPDQLTAKED VMETVPWFPK
101 KISDLDFCAN RVLLYGSELD ADHPGFKDNV YRRRRKYFAE LAMNYKHGDP
151 IPKIEFTEEE IKTWGTIFRE LNKLYPTHAC REYLRNLPLL SKYCGYREDN
201 IPQLEDVSNF LKERTGFSIR PVAGYLSPRD FLSGLAFRVF HCTQYVRHSS
251 DPLYTPEPDT CHELLGHVPL LAEPSFAQFS QEIGLASLGA SEETVQKLAT
301 CYFFTVEFGL CKQDGQLRVF GAGLLSSISE LKHALSGHAK VKPFDPKIAC
351 KQECLITSFQ DVYFVSESFE DAKEKMREFA KTVKRPFGLK YNPYTQSVQV
401 LRDTKSITSA MNELRYDLDV ISDALARVTR WPSV
```

Fig. 9

SEQUENCE LISTING

<160> NUMBER OF SEQ ID NOS: 1

<210> SEQ ID NO 1
<211> LENGTH: 434
<212> TYPE: PRT
<213> ORGANISM: homo sapiens

<400> SEQUENCE: 1

```
Met Thr Gly Pro Glu Thr Arg Ala Pro Ala Thr Trp Gln Ser Leu Ser
1               5                   10                  15

Gln Leu Pro Phe Asn Leu Phe Leu Ser Leu Thr Ser Leu Glu Asn His
                20                  25                  30

Val Ser Leu Leu His Ile Glu Ser Arg Lys Ser Lys Gln Arg Asn Ser
            35                  40                  45

Glu Phe Glu Ile Phe Val Asp Cys Asp Ile Ser Arg Glu Gln Leu Asn
        50                  55                  60

Asp Ile Phe Pro Leu Leu Lys Ser His Ala Thr Val Leu Ser Val Asp
65                  70                  75                  80

Ser Pro Asp Gln Leu Thr Ala Lys Glu Asp Val Met Glu Thr Val Pro
                85                  90                  95

Trp Phe Pro Lys Lys Ile Ser Asp Leu Asp Phe Cys Ala Asn Arg Val
                100                 105                 110

Leu Leu Tyr Gly Ser Glu Leu Asp Ala Asp His Pro Gly Phe Lys Asp
            115                 120                 125

Asn Val Tyr Arg Arg Arg Lys Tyr Phe Ala Glu Leu Ala Met Asn
        130                 135                 140

Tyr Lys His Gly Asp Pro Ile Pro Lys Ile Glu Phe Thr Glu Glu Glu
145                 150                 155                 160

Ile Lys Thr Trp Gly Thr Ile Phe Arg Glu Leu Asn Lys Leu Tyr Pro
                165                 170                 175

Thr His Ala Cys Arg Glu Tyr Leu Arg Asn Leu Pro Leu Leu Ser Lys
            180                 185                 190

Tyr Cys Gly Tyr Arg Glu Asp Asn Ile Pro Gln Leu Glu Asp Val Ser
        195                 200                 205

Asn Phe Leu Lys Glu Arg Thr Gly Phe Ser Ile Arg Pro Val Ala Gly
    210                 215                 220

Tyr Leu Ser Pro Arg Asp Phe Leu Ser Gly Leu Ala Phe Arg Val Phe
225                 230                 235                 240

His Cys Thr Gln Tyr Val Arg His Ser Ser Asp Pro Leu Tyr Thr Pro
                245                 250                 255

Glu Pro Asp Thr Cys His Glu Leu Leu Gly His Val Pro Leu Leu Ala
            260                 265                 270

Glu Pro Ser Phe Ala Gln Phe Ser Gln Glu Ile Gly Leu Ala Ser Leu
        275                 280                 285

Gly Ala Ser Glu Glu Thr Val Gln Lys Leu Ala Thr Cys Tyr Phe Phe
    290                 295                 300

Thr Val Glu Phe Gly Leu Cys Lys Gln Asp Gly Gln Leu Arg Val Phe
305                 310                 315                 320

Gly Ala Gly Leu Leu Ser Ser Ile Ser Glu Leu Lys His Ala Leu Ser
                325                 330                 335

Gly His Ala Lys Val Lys Pro Phe Asp Pro Lys Ile Ala Cys Lys Gln
            340                 345                 350

Glu Cys Leu Ile Thr Ser Phe Gln Asp Val Tyr Phe Val Ser Glu Ser
```

```
                    355                 360                 365
Phe Glu Asp Ala Lys Glu Lys Met Arg Glu Phe Ala Lys Thr Val Lys
        370                 375                 380

Arg Pro Phe Gly Leu Lys Tyr Asn Pro Tyr Thr Gln Ser Val Gln Val
385                 390                 395                 400

Leu Arg Asp Thr Lys Ser Ile Thr Ser Ala Met Asn Glu Leu Arg Tyr
                405                 410                 415

Asp Leu Asp Val Ile Ser Asp Ala Leu Ala Arg Val Thr Arg Trp Pro
                420                 425                 430

Ser Val
```

METHOD FOR DIAGNOSING NEURONAL DISEASES AND FOR TREATING PRIMARY HEMOSTASIS DEFICIENCY

This application is a 371 of PCT/DE01/03178 filed on Aug. 27, 2001, and claims benefit of Germany 10043/24,0 filed on Aug. 31, 2000.

BACKGROUND OF THE INVENTION

The present invention relates to a method for diagnosing neuronal diseases and or treating primary hemostasis deficiency. The invention further relates to a method for suppressing the immune system, which is inter alia significant for transplantation medicine and for the treatment of allergies. The invention is used in the field of medicine and pharmaceutical industry.

Several behavioral disorders, such as depressions, alcoholism, drug abuse, isomnia and nutritional disturbances, are disorders tightly connected to the central nervous system. The tissue hormone serotonin plays an essential role at many levels. Serotonin is a neurotransmitter inter alia for the stimulation of the peristalsis, vasodilatation and constriction (dosage depending), respectively, and the increase of the tonicity in the respiratory tract. It is not only a neurotransmitter in the CNS, but, in addition, a compound that can be found everywhere in the periphery, where serotonin was first discovered due to its activity as strong vascular constrictor (Rapport et al., J. Biol. Chem. 176:1237, 1948).

In addition, serotonin plays an essential role in primary hemostasis, that is, the inhibition of bleedings. The serotonin that is stored in the platelets is excreted at sites of vascular lesion, whereupon it interferes with the primary hemostasis (Holland, Proc. Soc. Exp. Biol. Med. 151:32–39, 1976).

Furthermore, the serotonin of the platelets further mediates between components of the immune system (Geba et al., J. Immmunol. 157:557–565, 1996). The mechanisms that thereby take place are yet unknown.

It is known that the enzyme tryptophan-hydroxylase (TPH), an enzyme that is expressed in neurons and pheripheric tissue, catalyses the yield-limiting step in the biosynthesis of serotonin, and is therefore essential for the function of the serotonergic system in the CNS and the periphery (Boadle-Biber, Prog. Biophys. Mol. Bio. 60:1–15, 1993).

There are already some medical applications, which rely on the effect of serotonin in the body. The increased release of serotonin by Rauwolfia-Alkoloides, and the retardation of the serotonin decay using MAO (Monoaminooxidase) inhibitors, respectively are used for the treatment of mental depressions, while its antagonist, methysergide, find its application in the treatment of migraine.

It has not yet been achieved to control the serotonin production in the body in such a manner that an effective treatment of the above-mentioned and other pathological phenomena are possible.

It is therefore an object of the invention to improve the diagnosis of neuronal diseases of the above-mentioned kind. It is a further or alternative object to develop agents for the treatment of the primary hemostasis deficiency as well as agents for suppressing the immune system based on new findings of the effect of serotonin.

SUMMARY OF THE INVENTION

The invention is based on the essential discovery that serotonin is synthesized in the body by TPH isoenzymes that are differently expressed in the neurons and the peripheric tissues. Gene targeting was used to show that an isoform, the peripheral enzyme (referred to in the following as TPH), is responsible for maintaining the primary hemostasis and T-cell mediated immune responses. Another isoform, the newly identified neuron specific TPH (referred to as nTPH) synthesizes serotonin independently thereof in the CNS.

Furthermore, some mechanisms could be elucidated. It was found
a) that the major step of serotonin in the primary hemostasis is mediated by the von Willebrand-factor. Furthermore, it was established that
b) the serotonin in the platelets is essential for the normal number of circulating $CD4^+$ cells, as well as for their normal activity, and thus provides a new target for an immune suppressive treatment.

In summary, it can be established that two separately regulated serotonergic systems exist in the CNS and the periphery which are defined by the peripheral isoform TPH and the neuronal isoform nTPH, respectively. This result is an important contribution for the use of these systems within the scope of the present invention.

BRIEF DESCRIPTION OF THE DRAWINGS

FIG. 1 shows the production of TPH(−/−)-mice.

FIG. 3 shows disturbed hemostasis in TPH(−/−)-mice.

FIG. 4 shows disturbed T-cell mediated immune responses in TPH(−/−)-mice.

DETAILED DESCRIPTION

The dichotomy of the serotonin-biosynthesis on the molecular level results in unexpected diagnostic and therapeutic possibilities. This relates to correlations between peripheric and central nervous serotonergic metabolites. In addition, this relates to possibilities of diagnostic fine-correlations, since the subtractive determination of the concentrations of the metabolites as present allows for the ascertainment of the CNS metabolites in the periphery. The peripheral serotonin-biosynthesis can thus transiently be inhibited specifically in order to subsequently determine the peripheral metabolite concentrations that stem from the CNS. The advantages of such a diagnostic method, in particular in the case of persisting psychiatric disorders, should outbalance the transient risk of bleeding episodes and distorted cell-mediated immune responses, since an improved therapy can follow after a more precise diagnosis.

The invention primarily relates to inhibitors or promoters, respectively of both TPH-isoforms which can be used for diagnosing neuronal diseases and for treating primary hemostasis deficiency. Furthermore, the invention relates to the use of these inhibitors for suppressing the immune system, which is of importance inter alia for transplantation medicine and for the treatment of allergies.

The method is characterized by a modulation of the regulation of nTPH and/or TPH and thus the specific serotonin production in the body. It was shown that the peripheral TPH is essential for primary hemostasis and for the T-cell-mediated immune response, whereas the newly identified nTPH, which is independently expressed and synthesizes serotonin in the CNS is responsible for the serotonergic effects in behavioral physiology. This results in new pharmacological possibilities for immune suppression and for the therapeutic manipulation of hemostasis.

The modulation of the nTPH- and/or TPH-regulation takes place in the following ways:

Specific inhibitors of the peripheral TPH-isoforms were developed that rely on the molecular differences of the TPH-isoforms as described, and also inhibitors that cannot pass the blood-brain-barrier. Specific inhibitors for the TPH-isoforms can be found in vitro using fairly simple screening methods, since the cDNAs of the two isoforms that were obtained can be used for the specific expression of the pure isoforms using expression systems. These inhibitors, in addition to a diagnostic use, account also for therapeutical uses, since increased serotonin levels in the blood are found in a plurality of complications.

a) In this context it is worth mentioning that during the use of SSRI (serotonin specific reuptake inhibitors)-antidepressive agents in the psychopharmacological therapy, as side effects in some cases serious bleeding complications became known (Goldberg, Arch. Fam. Med. 7:78–84, 1998). These side effects can be traced back to the decreased serotonin-level in platelets due to said therapy (Bottlender et al., Fortschr. Neurol. Psychiatr. 66:32–35, 1998). Also associated with this field of application are the new findings of the participation of serotonin in primary hemostasis. One side effect of antidepressive agents which act in a blocking fashion on the serotonin-transporter is the incidence of acute bleeding episodes, apparently due to the insufficient serotonin storage in the thrombocytes of the patients that are treated. That is to say that the serotonin-transporter of the thrombocytes is identical with the specific target of the antidepressive agents, the serotonin-transporter of the CNS. In the case of such bleeding episodes the antidepressants are usually displaced, which results in a decline of the status of the afflicted patients and an increase of the depression-induced risk for suicide. This can be avoided if commercially available von Willebrand-factor (vWF) is infused during such an acute bleeding episode.

b) Increased serotonin-concentrations during the pre-eclampsia correlate with the increase of the $CD4^+$-T-cell-subpopulations. Using specific inhibitors of the peripheral TPH-isoform, an early treatment of the imminent pre-eclampsia is enabled, which neither exerts an influence on the serotonin-biosynthesis in the maternal nor in the fetal brain.

c) In addition to these applications, a positive influence of only peripherally acting inhibitors on transplantation medicine also can be achieved. An essential limitation in a common immune suppressive therapy is given by the nephro-, hepato- and neurotoxic side effects of the most commonly used substance clyclosporin A (CsA). More recent immune suppressants of natural origin, such as FK506 and rapamycin in combination preparations together with CsA thus allow a more effective (additive) immune suppresive treatment having lower side effects, since CsA is thus applied at a lower dosage.

The immune suppressive effect of lowered serotonin levels in the blood can be used in order to apply toxic substances, CsA, FK 506, and rapamycin, at a lower dose.

According to the invention, the manipulation of the nTPH- and/or TPH-regulation can take place in the following ways:

The specific down-regulation of nTPH and/or pTPH using molecular biology takes place with ribozymes, antisense-oligonucleotides or by antisense-RNA-expression, wherein the differences in the sequences of the isoform-mRNAs allow for the modulation of only one of each mRNA at once. In addition, according to the invention, also pharmacological preparations are employed using specific TPH-inhibitors, such as, for example, p-chlorophenylalanine or p-ethynylphenylalanine.

The serotonin production is preferably stimulated by tissue specific over-expression of the TPH-isoforms using molecular biology. Pharmacologically, for example, the precursor-compound 5-hydroxytryptophan, and also substituted analogues, and, last but not least, also serotonin itself can be administered.

The method according to the present invention for diagnosing neuronal diseases is characterized in that a specific inhibition of the peripheral serotonin-biosynthesis is performed, subsequently the metabolite concentrations derived from the CNS are determined, and based on a comparative curve the grade of the disease is ascertained. For this, it is required to use compounds that cannot pass the blood-brain-barrier.

Figure 9:
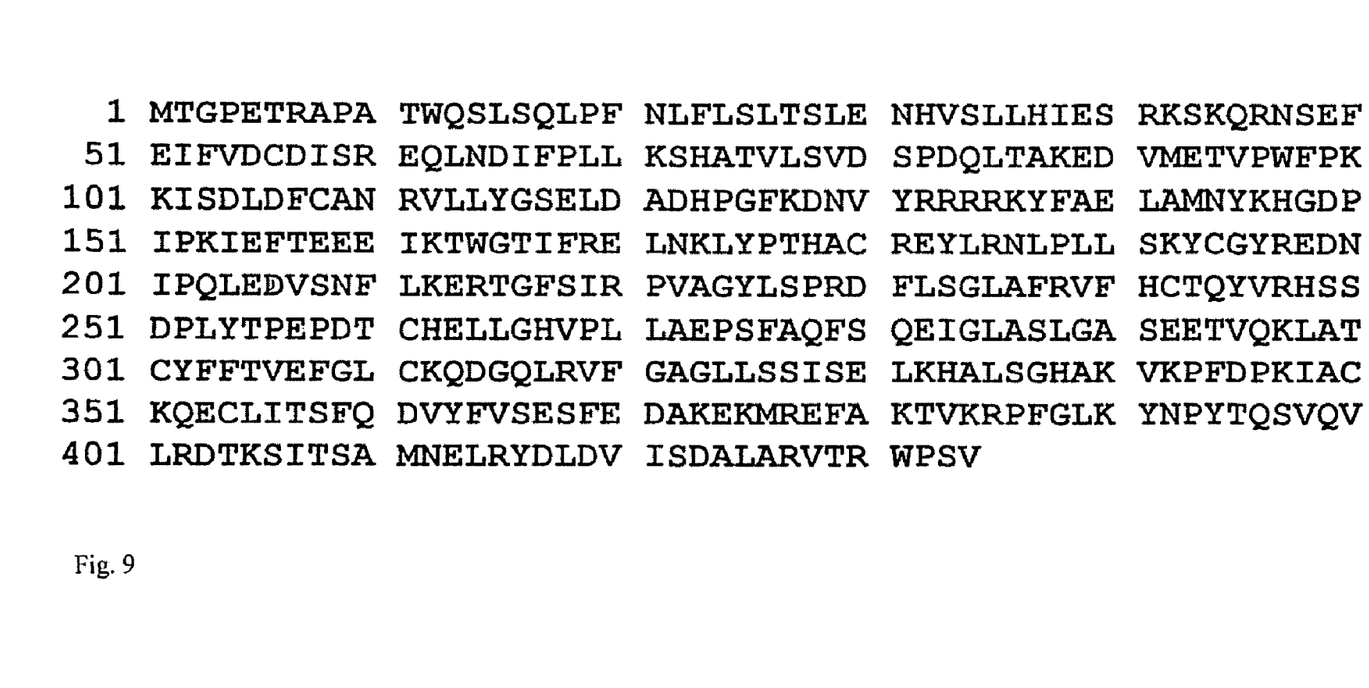
FIG. 9 shows the amino acid sequence of nTPH.

The invention further relates to the newly identified neuronal tryptophan-hydroxylase (nTPH) that differs from the known TPH its regulatory domain (the catalytic domain is identical). nTPH has the amino acid sequence, that is depicted in FIG. 9.

Figure 1:
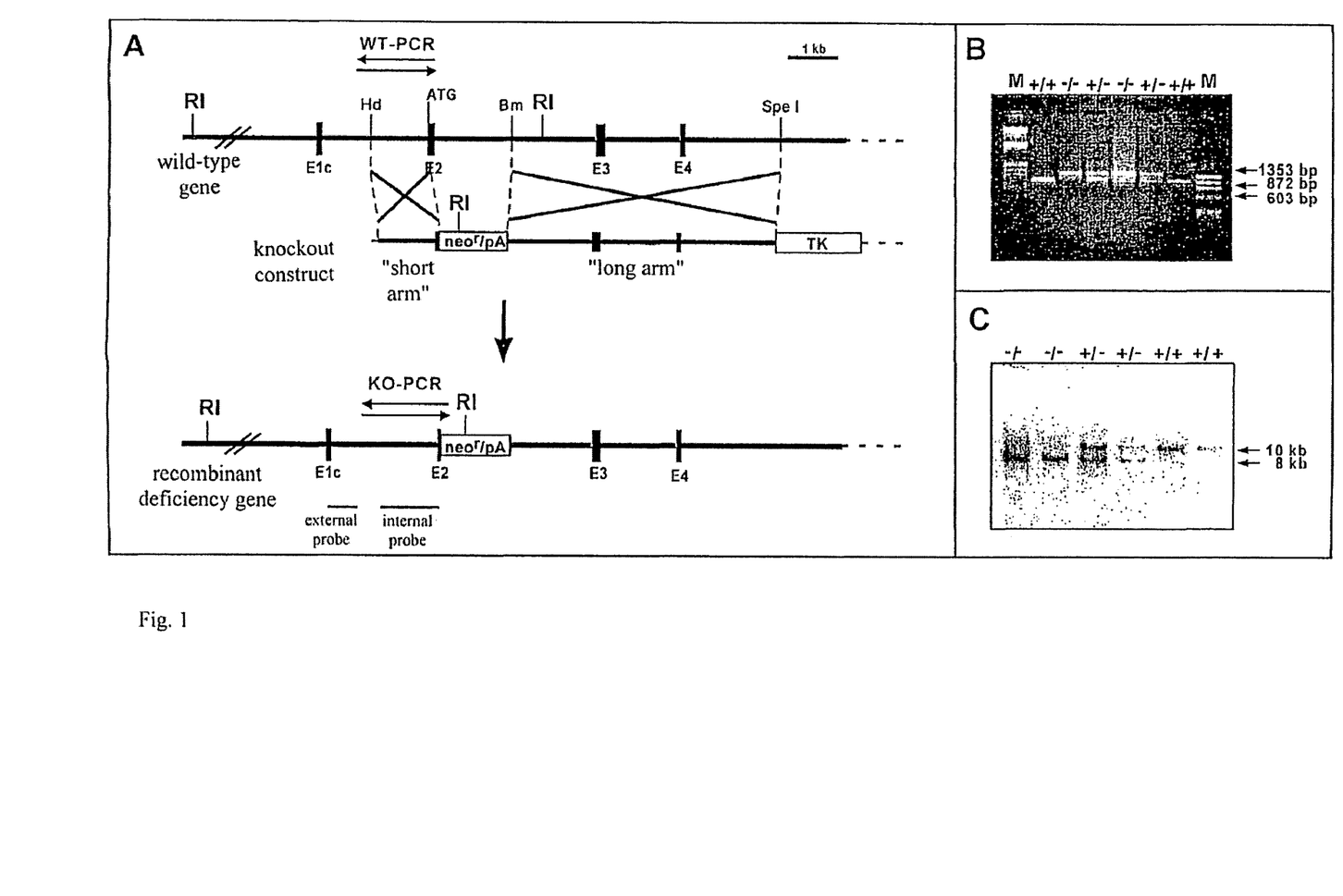

The invention shall be described in detail in the following based on embodiments (figures), in which:

FIG. 1. Production of TPH(−/−)-mice

A. Schematic representation of the targeting-method. The first four of the 11 exons of the TPH-gene are depicted. The knock-out construct was integrated by homologous recombination in one allele of the ES-cells, whereby the first coding exon of the TPH-gene was inactivated. Furthermore, the integrated neomycin resistance-cassette contained a transcriptional-stop-sequence. The positions of the analytic amplicons are depicted for wild-type and knock-out-indentification, as well as the positions of the internal and external Southern blot probes. Identical Eco-RI-sites that enable the identification of wild-type and knock-out-animals in Southern blots are depicted in bold (RI). Restriction sites: RI: Eco RI; Hd: Hind III; Bm: Bam HI; Sc:Sac I.

B. Agarose gel-electrophoresis of analytical PCR-products. As stated in A, a 1.1 kb-fragment for the wild-type-allele, and a 1.3 kb-fragment for the knock-out-allele is obtained, respectively.

C. Southern blot-examination of Eco RI-digested genomic DNA. As stated in A, both probes detect a 10 kb-fragment for the wild-type allele and an 8 kb-fragment for the knock-out-allele.

Figure 2:
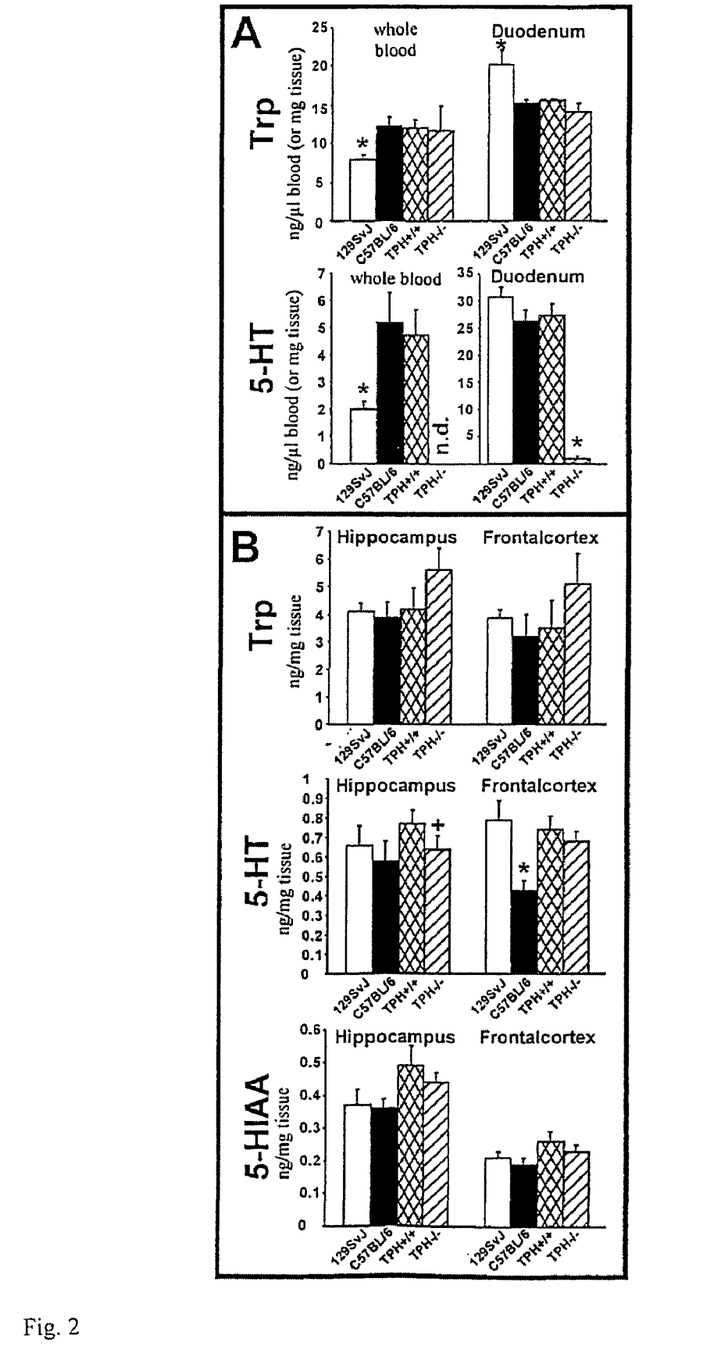
FIG. 2 shows the quantification of tryptophan (Trp) and serotonin (5-HT) in peripheral tissues and of Trp, 5-HT and 5-hydroxyindoleacetic acid (5-HIAA) in selected areas of the brain.

FIG. 2. Quantification of trypthophan (Trp) and serotonin (5-HT) in peripheral tissues and of Trp, 5-HT and 5-hydroxyindoleacetic acid (5-HIAA) in selected areas of the brain.

A. Trp and 5-HT in whole blood and in duodenum-samples of 129SvJ-, C57BL/6-, TPH(−/−)-, and TPH(+/+)-mice. N.d: not detectable (<25 fg/µl). *: statistically significant compared to all other mice-straines ($p<0.05$).

B. Trp, 5-HT and 5-HIAA in hippocampus- and frontal cortex-samples of 129SvJ-, C57BL/6-, TPH(−/−)-, and TPH(+/+)-mice. *: statistically significant compared to all other mice-strains ($p<0.05$). 5-HT is significantly lowered in the hippocampus of TPH(−/−)-mice compared with TPH(+/+)-mice, nevertheless not compared with the other laboratory-mice-strains.

Figure 3:
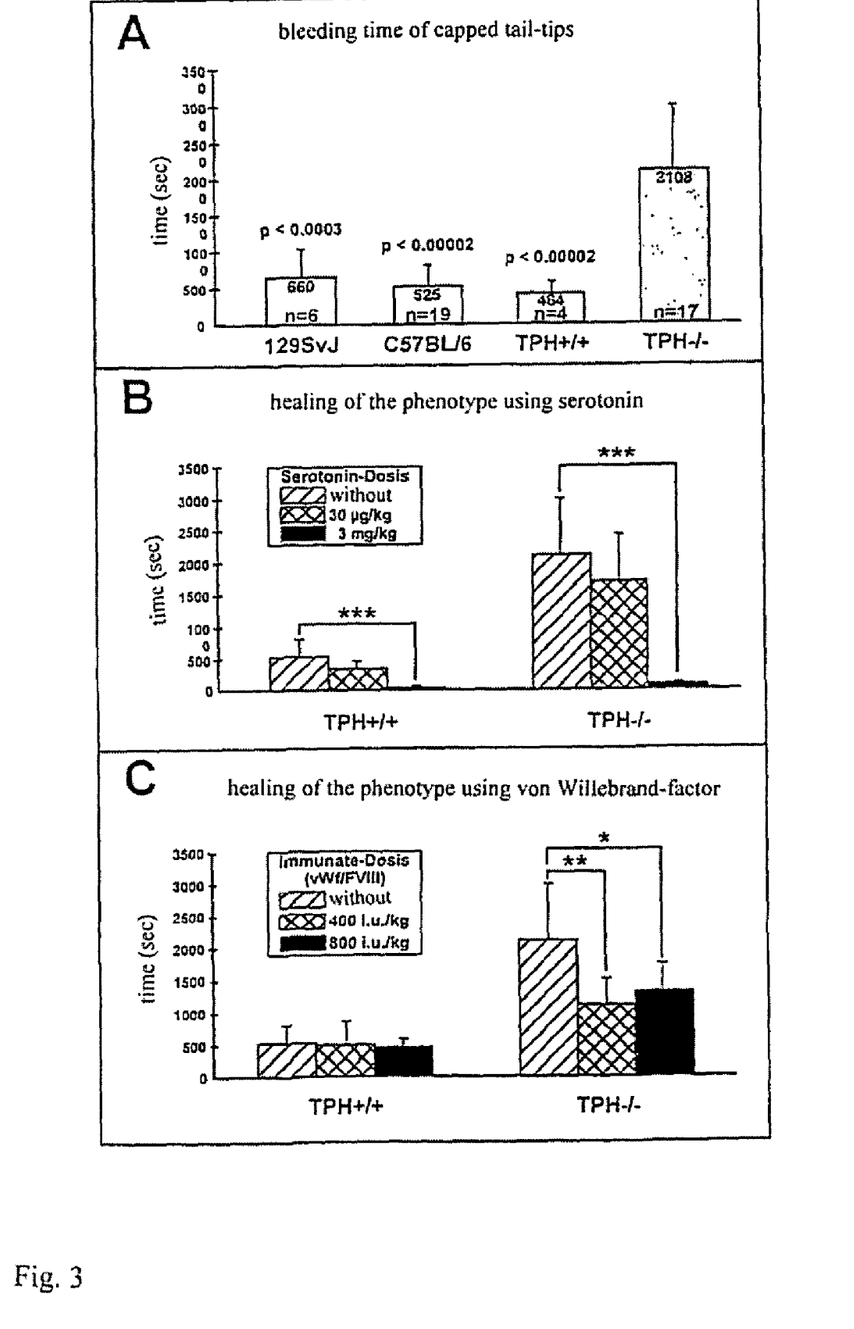

FIG. 3. Disturbed hemostasis in TPH(−/−)-mice.

A. Prolonged bleeding times of TPH(−/−)-animals. Normal bleeding times of control-animals are at 8-11 min, whereas TPH(−/−)-mice bleed at an average of 35 min.

B. Healing of the phenotype by intracardial 5-HT-injection. The 5-HT-amounts applied result in ¹⁄₁₀ and the ten-fold of the normal blood concentrations.

C. Healing of the phenotype by intracardial von Willebrand-factor injection. The effect is specific for the TPH(−/−)-mice, whereas control-animals are not affected.

Figure 4:
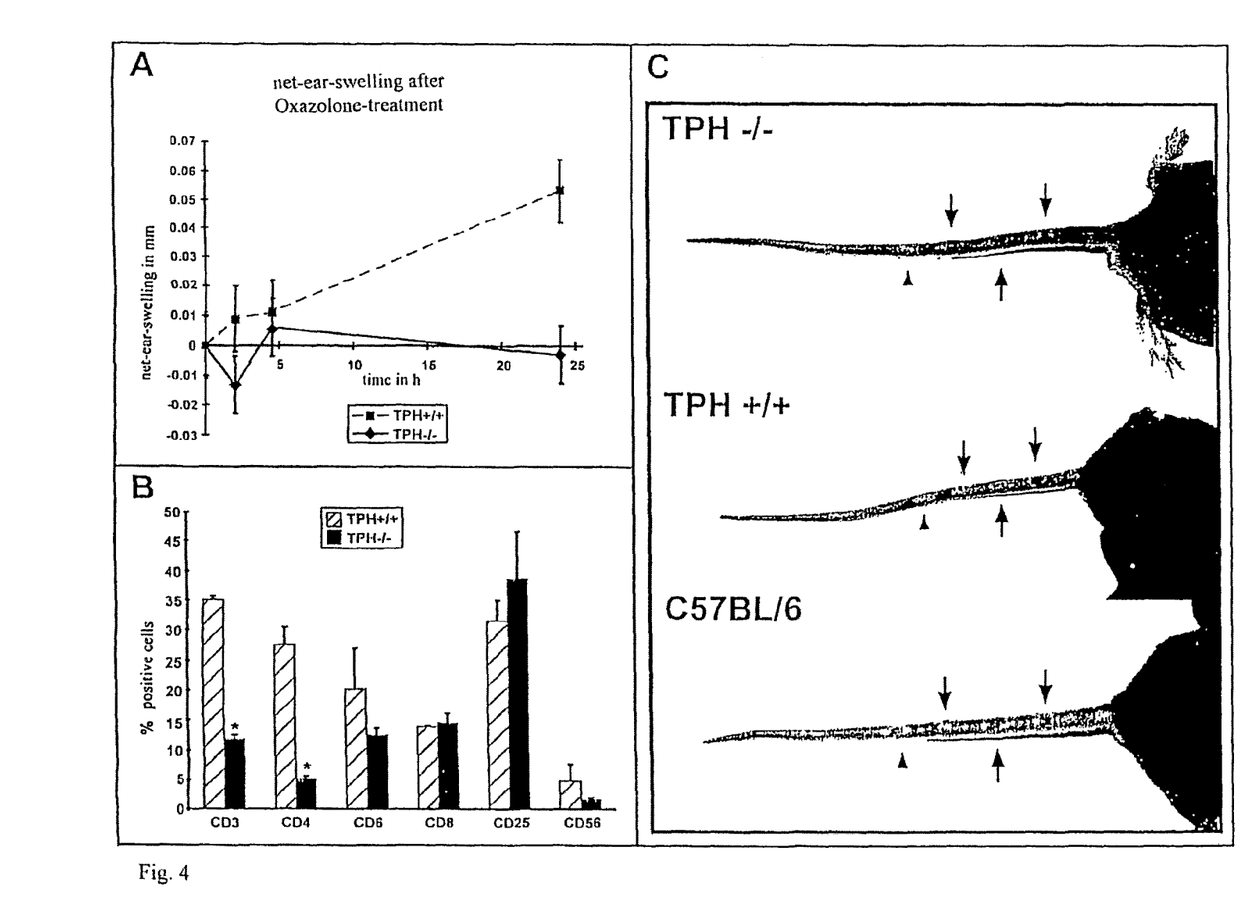

FIG. 4. Disturbed T-cell-mediated immune responses in TPH(−/−)-mice.

A. Time course of the net swelling of ears after oxazolone treatment, indicative for T-cell-mediated hypersensitivity of the late type. TPH(−/−)-mice do not exhibit an allergic swelling reaction.

B. Determination of leucocyte-subpopulations in the peripheral blood of TPH(−/−)-animals using flow-cytometry. Only CD+4-T-cells (CD4+/CD3+) are significantly reduced ($p<0.05$), but not CD8+-T-cells.

C. Exemplary illustration of the rejection of skin-second-order-transplants. Arrowheads indicate the sensitizing transplants of the first order, arrows the transplants of the second order. In comparison with the well-healing transplants on TPH(−/−)-animals, the transplants on TPH(+/+)- and C57BL/6-animals can at the outer edges of wounds (white rejection) be identified by insufficient revascularization and infections at the same time or are already completely rejected (transplant of first order and two of the transplants of second order on the C57BL/6-animal).

Figure 5:
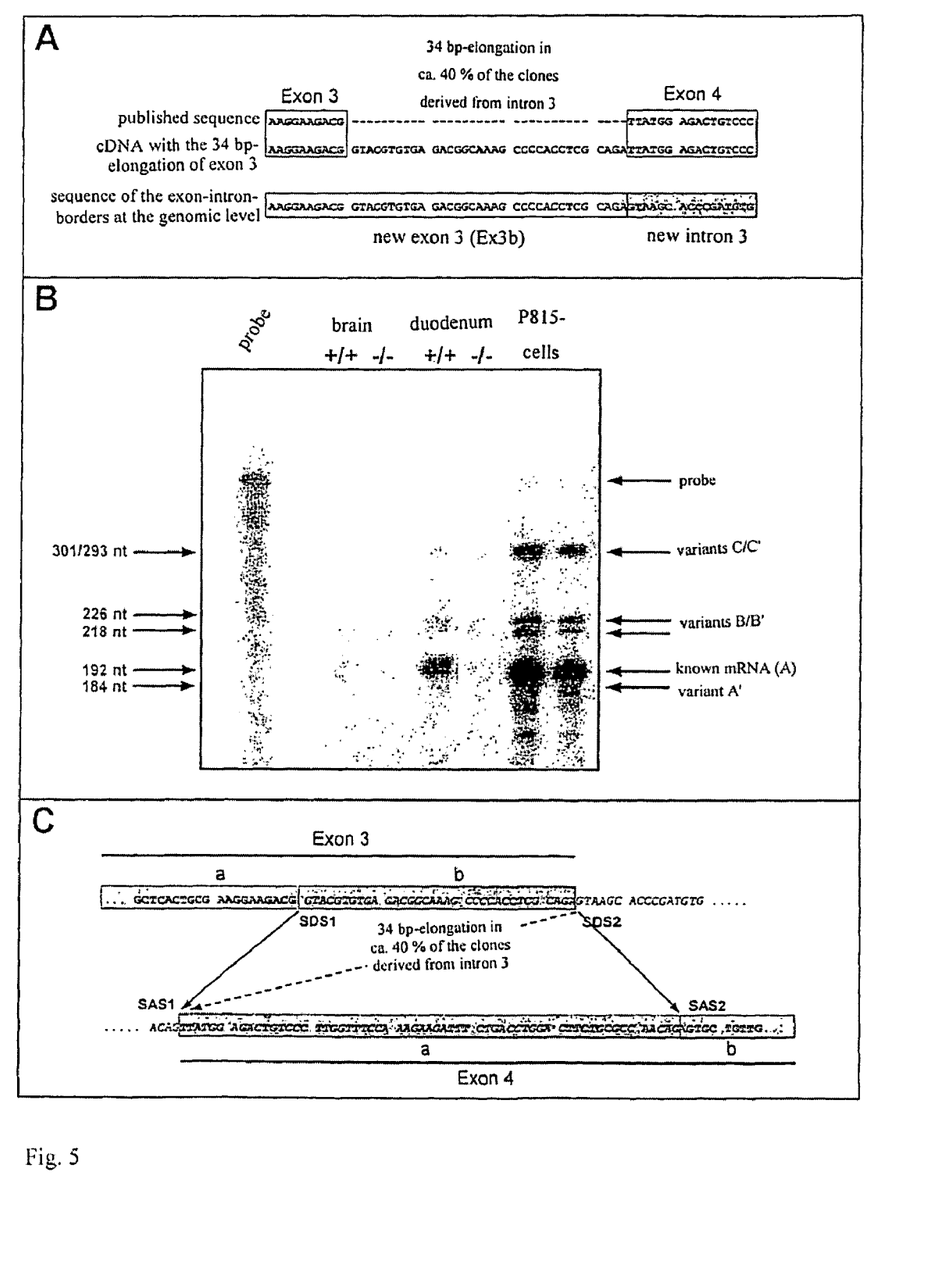
FIG. 5 illustrates the complexity of TPH-expression in a mouse.

FIG. 5. Complexity of TPH-expression in the mouse.

A. Sequence alignment of the published cDNA (Stoll et al., 1990) of the cloned alternatively spliced cDNA having a 34 bp-elongation of exon 3 and genomic DNA. Chromosomal DNA has the 34 bp-elongation directly after the splicing-donor-site of exon 3, whereupon an obligatory GT-dinucleotide follows; the elongated exon 3 is in the following designated exon 3b.

B. RNase protection assays of 80 μg total-RNA of the organs as indicated and 10 μg of the mastocytoma-cells P815 (2x) with the cDNA described in 5A. The probe clearly identifies six splice variants of the mouse-TPH-mRNA. It has to be noted that only a set of three variants is expressed in the TPH-KO-mice. The weak band at the position of the known TPH-mRNA that can be seen in the duodenum and lung of TPH-KO(−/−)-animals results from a high sequence homology of the variants. The P815-RNAs show how comparatively low the expression of TPH is in tissues, namely nearly at the level of detectability.

Figure 7:
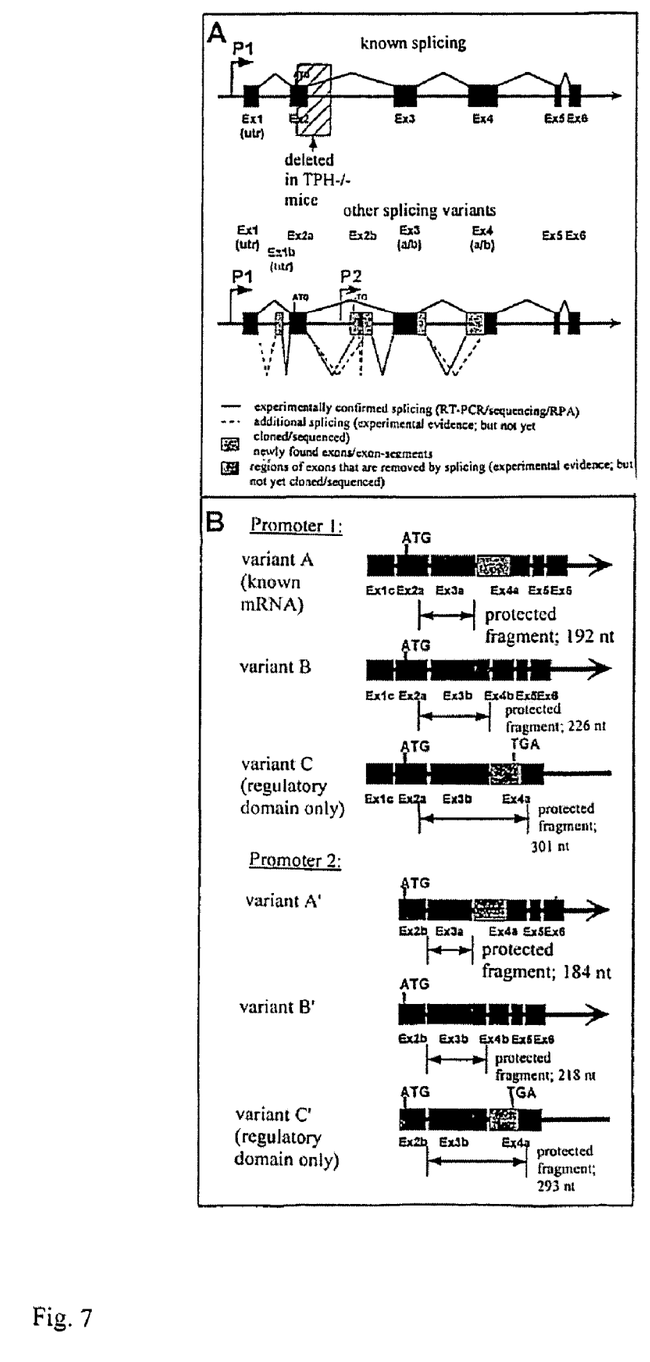
FIG. 7 is a schematic representation of TPH gene structure.

C. Alternative splicing between exon 3 and exon 4. The splicing-donor-(SDS)- and splicing-acceptor-sites (SAS) that are involved are indicated. The parts of the sequence of the published sequence are marked as exon 3a and exon 4a. Splicing of SDS2 on SAS 1 results in the C-variants, which only code for the regulatory domain of the TPH-isoforms (cf. FIG. 7B). The splicing of SDS2 on the internal SAS2 of exon 4 eliminates the frame shift that would be the result of the additional 34 bp of exon 3b. The constant regions are shaded in light grey, the alternative segments in dark grey. Furthermore, the alternative segments as well as flanking intron-sequences are indicated in italic.

Figure 6:
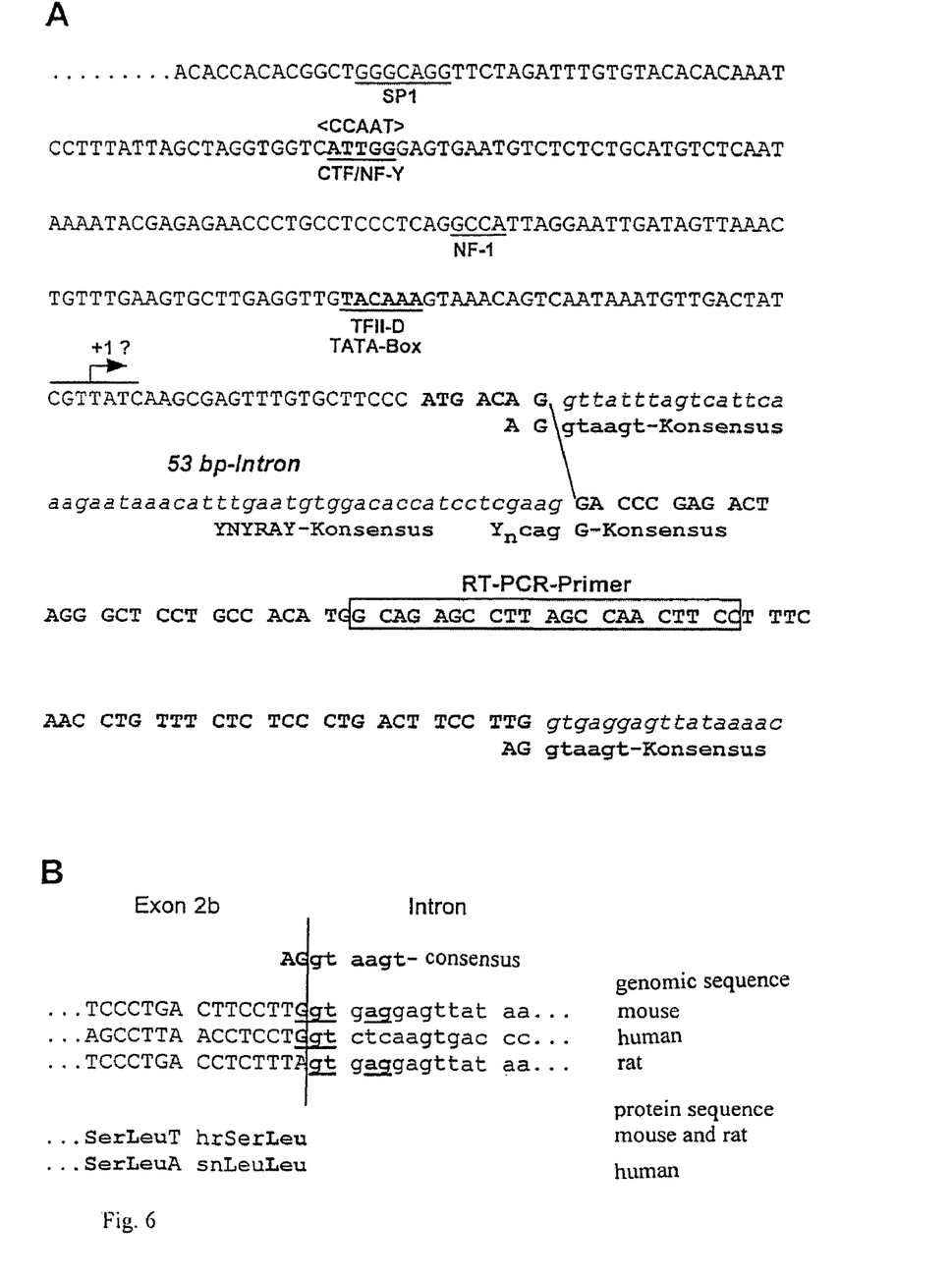
FIG. 6 shows the characterization of a new exon 2b in mice.

FIG. 6. Characterization of the new exon 2b

A. Genomic sequence of exon 2b of the mouse with flanking sequences. The ORF in the trinucleotide-notation is marked in bold. In the 5'-flanking region, a part of the putative new promoter is shown, wherein one TATA-box and the most probable start of transcription (+1) are indicated. In the 3'-region, the splicing-donor-site of exon 2b is depicted. Intron-sequences have been indicated in small letters in italic, wherein the short intron of 53 bp was symbolically bridged from the segments of the ORF using a line. For clarity, the respective consensus-sequences are indicated below the splicing-donor-sites,-branching-sites, and -accepting-sites, respectively that are involved.

B. Examination of the exon-intron-structure of the new exon 2. Five out of eight nucleotides in the mouse are identical with the consensus-sequence of splicing-donor-sites (bold and underlined), four in the rat and three in human. The intron between the new exon 2 and exon 3 has an exact length of 948 bp in the mouse, similarly as in rat and in human.

FIG. 7. Schematic depiction of the TPH-gene-structure

A. Schematic comparision of the known splicing-structure (top) with the structure that was obtained in the present work for the gene segments of the regulatory domain (bottom). The promoter position that is supported by experimental evidence, was marked with P2.

B. Assembly of all newly discovered mRNA-variants. The promoter 1 is primarily active in the periphery, whereas the new promoter 2 is responsible for expression in CNS.

The mRNA that is indicated as variant A is the known form of the TPH-mRNA. The variant A' was already cloned and codes for an active TPH-Isoform. The variants B and B' are not yet cloned, nevertheless, they have been clearly identified for several times now using RPA-assays. Variants C and C' lead to the expression of only the regulatory domains. For clarity, the mRNAs are only depicted up to the $6^{th}$ exon of the overall 11 exons.

Figure 8:
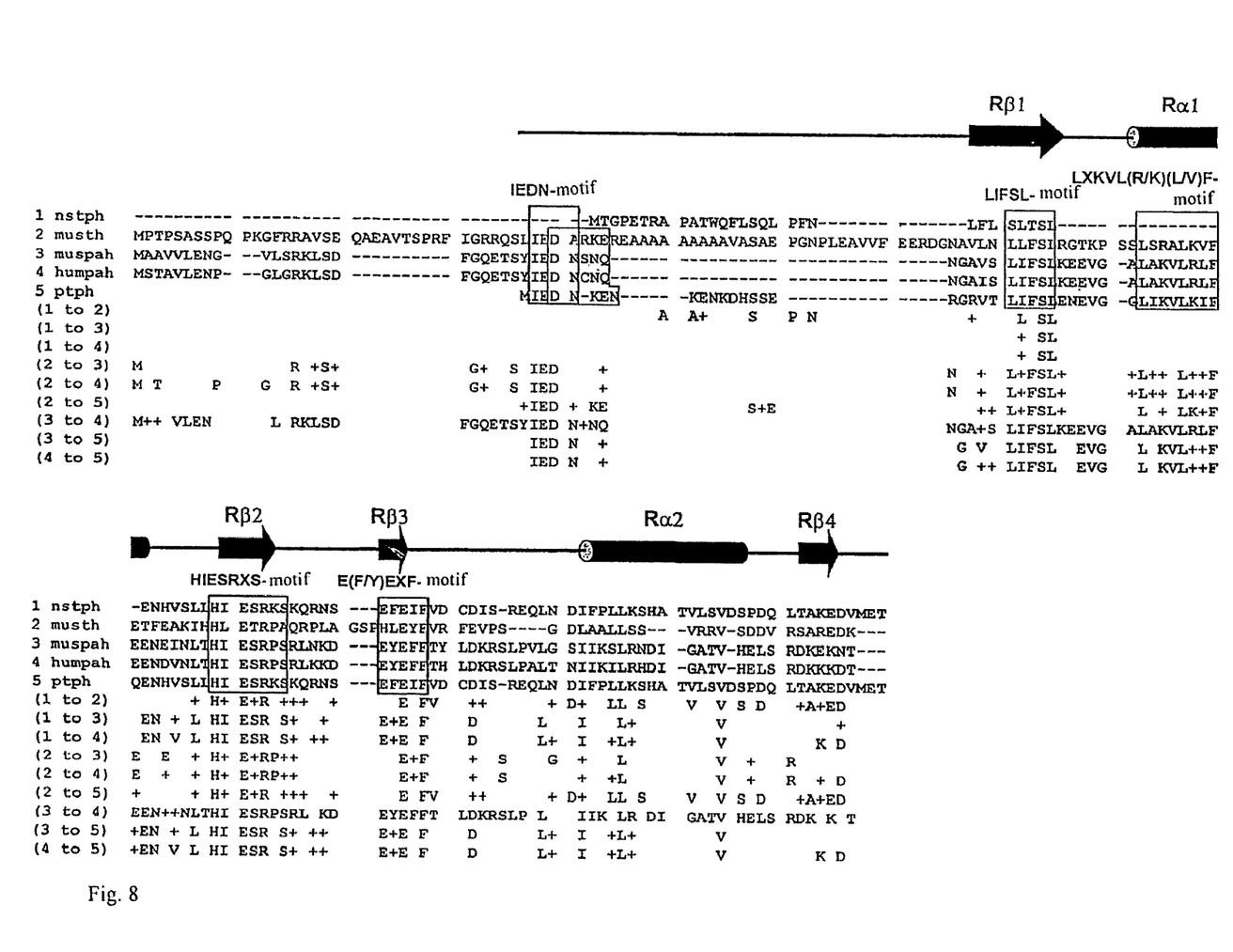
FIG. 8 shows the amino acid-sequence alignment of a new regulatory domain of TPH with other AAAHs.

FIG. 8. Amino acid-sequence-alignment of the new regulatory domain of TPH with other AAAHs The upper part of the sequences shows the new segment of TPH. Below, the conserved parts of the sequence of the regulatory domains of the AAAHs are indicated. The sequences have each been aligned with another using the clustal W-program and have been assembled manually. In doing so, larger gaps were partially allowed in order to indicate the identical structural elements. Noticeable sequence motifs are framed and individually named. Four of the five motifs are identical with elements of the secondary structure of the PAH. Overlapping in part with the IEDN-motif, a region of the regulatory domain is framed and shaded in gray that reaches into the groove of the catalytic centre, as it is known from christallographic examinations of the PAH. Further explanations in the text. The sequences used are: nstph=neuron-specific TPH (the new variant) of the mouse, musth=TH of the mouse, muspah and humpah=murine and human PAH, ptph=peripheral TPH of the mouse (known variant).

FIG. 9. Amino acid-sequence of the nTPH

What is claimed is:

1. A pharmaceutical composition for the treatment of primary hemostasis deficiency, comprising:
an agent that acts on the level of serotonin in the blood selected from the group consisting of p-chlorophenylalanine, p-ethynylphenylalanine, serotonin, 5-hydroxyindoleacetic acid (5-HIAA), 5-hyroxytryptophan, substituted analogues of 5-hydroxytryptophan, von Willebrand-factor and combinations thereof, wherein said composition further comprises a pharmaceutically acceptable diluent, a pharmaceutically acceptable carrier or combinations thereof.

2. The pharmaceutical composition as recited in claim 1, further comprising an antidepressive agent that acts on the level of serotonin in the body.

3. The pharmaceutical composition as recited in claim 1, wherein the agent that acts on the level of serotonin in the blood can not pass through the blood-brain barrier.

4. The pharmaceutical composition as recited in claim 1, wherein the agent that acts on the level of serotonin in the blood is selected from the group consisting of 5-hydroxytryptophan, substituted analogues of 5-hydroxytryptophan, serotonin, von Willebrand-factor (vWF) and combinations thereof.

5. A method for treatment of primary hemostasis deficiency in a mammal in need of treatment, comprising: administering to the mammal in need of treatment an effective amount of a pharmaceutical composition as recited in claim 1.

6. The method for treatment of primary hemostasis deficiency in a mammal in need of treatment as recited in claim 5, wherein the mammal is a human.

7. A method for treatment of a depressive disorder in a mammal in need of treatment, comprising administering to the mammal in need of treatment an effective amount of a pharmaceutical composition as recited in claim 2.

8. The method for the treatment of a depressive disorder in a mammal as recited in claim 7, wherein the mammal is a human.

* * * * *

UNITED STATES PATENT AND TRADEMARK OFFICE
CERTIFICATE OF CORRECTION

PATENT NO. : 7,049,336 B2
APPLICATION NO. : 10/363474
DATED : May 23, 2006
INVENTOR(S) : Diego Walther and Michael Bader It is certified that error appears in the above-identified patent and that said Letters Patent is hereby corrected as shown below:

On Title Page
item (73) Assignee:
"Molekularc" should read --Molekulare--.

Signed and Sealed this

Twelfth Day of September, 2006

JON W. DUDAS
*Director of the United States Patent and Trademark Office*